United States Patent
Ito

(10) Patent No.: US 11,149,010 B2
(45) Date of Patent: Oct. 19, 2021

(54) PRODUCING METHOD FOR 3-DIFLUOROMETHYLPYRAZOLE COMPOUND, PRODUCING METHOD FOR 3-DIFLUOROMETHYLPYRAZOLE-4-CARBOXYLIC ACID COMPOUND, AND PYRAZOLIDINE COMPOUND

(71) Applicant: FUJIFILM Corporation, Tokyo (JP)

(72) Inventor: Takayuki Ito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/098,466

(22) Filed: Nov. 16, 2020

(65) Prior Publication Data

US 2021/0061766 A1 Mar. 4, 2021

Related U.S. Application Data

(63) Continuation of application No. PCT/JP2019/018348, filed on May 8, 2019.

(30) Foreign Application Priority Data

May 18, 2018 (JP) .............................. JP2018-096387

(51) Int. Cl.
*C07D 231/14* (2006.01)
*C07D 231/04* (2006.01)

(52) U.S. Cl.
CPC ......... *C07D 231/14* (2013.01); *C07D 231/04* (2013.01)

(58) Field of Classification Search
CPC ........................... C07D 231/14; C07D 231/04
See application file for complete search history.

(56) References Cited

U.S. PATENT DOCUMENTS

| | | | |
|---|---|---|---|
| 8,115,006 B2 | 2/2012 | Koyanagi et al. | |
| 8,188,295 B2 | 5/2012 | Nett et al. | |
| 2008/0188442 A1 | 8/2008 | Lamberth et al. | |
| 2010/0292236 A1 | 11/2010 | Li et al. | |
| 2011/0288304 A1 | 11/2011 | Pazenok et al. | |
| 2015/0005293 A1 | 1/2015 | Li et al. | |
| 2015/0239846 A1 | 8/2015 | Pazenok et al. | |
| 2018/0362512 A1 | 12/2018 | Guisot | |
| 2019/0000806 A1 | 1/2019 | Guisot | |

FOREIGN PATENT DOCUMENTS

| | | |
|---|---|---|
| JP | 2009013158 | 1/2009 |
| JP | 2009501742 | 1/2009 |
| JP | 2010533736 | 10/2010 |
| JP | 2013530945 | 8/2013 |
| JP | 2015529658 | 10/2015 |
| WO | 2004033432 | 4/2004 |
| WO | 2008152138 | 12/2008 |
| WO | 2009106619 | 9/2009 |
| WO | 2010009990 | 1/2010 |
| WO | 2015003289 | 1/2015 |
| WO | 2016158716 | 10/2016 |
| WO | 2017103611 | 6/2017 |

OTHER PUBLICATIONS

"International Search Report (Form PCT/ISA/210) of PCT/JP2019/018348," dated Jul. 16, 2019, with English translation thereof, pp. 1-5.
"Written Opinion of the International Searching Authority (Form PCT/ISA/237) of PCT/JP2019/018348," dated Jul. 16, 2019, with English translation thereof, pp. 1-7.
Werner Fliege, et al., "1,3-Dipolare Cycloadditionen, 91. Die Chemie des N-Methyl-C-phenylnitrilimins," Chemische Berichte, vol. 117, Mar. 1984, pp. 1194-1214.
Arthur G.Schultz, et al., "Aromatic Ring Synthesis by N-Aminopyrrole Diels-Alder Reaction. Characterization of the Heteroatom Fragment," Tetrahedron Letters, vol. 22, Dec. 1981, pp. 1767-1770.
"Office Action of Japan Counterpart Application", dated Aug. 24, 2021, with English translation thereof, pp. 1-12.

*Primary Examiner* — Kamal A Saeed

(74) *Attorney, Agent, or Firm* — JCIPRNET

(57) ABSTRACT

Provided are producing methods for a 3-difluoromethylpyrazole compound and a 3-difluoromethylpyrazole-4-carboxylic acid compound, which include, in a reaction solvent containing a specific solvent, subjecting a difluoroacetyl group-containing compound, a hydrazine compound, and formaldehyde to a cyclocondensation reaction, and subsequently oxidizing the obtained pyrazole compound precursor, and a pyrazolidine compound represented by a specific formula in these producing methods.

8 Claims, No Drawings

PRODUCING METHOD FOR 3-DIFLUOROMETHYLPYRAZOLE COMPOUND, PRODUCING METHOD FOR 3-DIFLUOROMETHYLPYRAZOLE-4-CARBOXYLIC ACID COMPOUND, AND PYRAZOLIDINE COMPOUND

This application is a Continuation of PCT International Application No. PCT/JP2019/018348 filed on May 8, 2019, which claims priority under 35 U.S.C. § 119 (a) to Japanese Patent Application No. 2018-096387 filed in Japan on May 18, 2018. Each of the above applications is hereby expressly incorporated by reference, in its entirety, into the present application.

BACKGROUND OF THE INVENTION

1. Field of the Invention

The present invention relates to a producing method for a 3-difluoromethylpyrazole compound and a producing method for a 3-difluoromethylpyrazole-4-carboxylic acid compound. In addition, the present invention relates to a pyrazolidine compound obtainable in the processes of the producing methods above.

2. Description of the Background Art

A compound having a heterocyclic ring structure (hereinafter, referred to as "heterocyclic compound") is often found in a natural product and a biological component, and has unique chemical properties, and thus has been applied to various uses. For example, it is used as an active ingredient (physiologically active substance) of a medicine or an agricultural chemical, and as a functional material of a liquid crystal material, an organic semiconductor, or the like. Among the heterocyclic compounds, a pyrazole compound having a pyrazole ring structure in which two nitrogen atoms are adjacent to each other is useful as an active ingredient of a medicine, agricultural chemical, or the like, and also as synthetic intermediates thereof.

For example, as the pyrazole compound useful as an active ingredient of an agricultural chemical, 3-difluoromethyl-1-alkyl-1H-pyrazole-4-carboxylic acid or a carboxylic acid derivative (for example, an acid halide, an acid anhydride, and a carboxylic acid ester, a carboxylic acid amide, and a nitrile) are mentioned. The producing (synthesizing) method for this compound includes known methods (WO2009/106619A and WO2010/009990A) in which ethyl 2-ethoxymethylene-4,4-difluoro-3-oxobutanoate obtained by reacting ethyl 4,4-di fluoroacetoacetate with triethoxymethane is cyclized using methylhydrazine. In addition to these methods, for example, WO2008/152138A proposes a method in which an iminium salt obtained by reacting 1,1,2,2-tetrafluoroethyldimethylamine with boron trifluoride and methyl 3-methoxyacrylate is cyclized using methylhydrazine. Further, WO 2016/158716A proposes a method in which difluoroacetoacetic acid ester is reacted with 1-formyl-1-methylhydrazine.

As a promising synthetic intermediate for a pyrazole compound, dihydropyrazole compounds (pyrazoline compounds) such as 3-difluoromethyl-1-methyl-4,5-dihydro-1H-pyrazole-4-carboxylic acid and a carboxylic acid derivative thereof are mentioned. It is known that such a dihydropyrazole compound can be synthesized by heating ethyl 4,4-difluoroacetoacetate, formalin, and methylhydrazine in ethanol in the presence of an acid catalyst (JP2009-501742A).

As a method for synthesizing a pyrazole compound from a dihydropyrazole compound, for example, an oxidation reaction of a dihydropyrazole compound with an oxidizing agent such as a persulfuric acid, chloranil, or nickel (IV) oxide is known (JP2009-013158A, Chem. Ber., 117 (1984), p. 1194-1214, and Tetrahedron Let., 22 (1981), p. 1767-1770).

SUMMARY OF THE INVENTION

In the conventional producing methods for the above-mentioned pyrazole compound and dihydropyrazole compound, there is room for improvement, for example, regarding the facts that compounds that are difficult to be available or expensive compounds are used as raw materials, severe reaction conditions are required, the yield is not sufficient, and the like. Specifically, according to the producing method in JP2009-501742A, 3-difluoromethyl-1-methyl-4,5-dihydro-1H-pyrazole-4-carboxylic acid ethyl ester can be obtained only in a low yield of about 24%.

In consideration of the above circumstances, an object of the present invention is to provide a producing method for 3-difluoromethylpyrazole compound, in which the targeted 3-difluoromethylpyrazole compound can be produced in good yield and high selectivity with simple operation under mild conditions, using relatively inexpensive and easily available compounds as raw materials. In addition, another object of the present invention is to provide a producing method for a 3-difluoromethylpyrazole-4-carboxylic acid compound through the producing method for a 3-difluoromethylpyrazole compound. Further, another object of the present invention is to provide a pyrazolidine compound as a synthetic intermediate in the producing method for a 3-difluoromethylpyrazole compound.

As a result of various studies, the inventors of the present inventions have found that, by oxidizing a pyrazole compound precursor prepared by cyclocondensing a specific difluoroacetyl group-containing compound, a hydrazine compound, and formaldehyde in a reaction solvent containing a specific solvent, it is possible to synthesize, even under mild reaction conditions, a 3-difluoromethylpyrazole compound and further a 3-difluoromethylpyrazole-4-carboxylic acid compound in good yield, while suppressing the generation of by-products such as isomers. The present invention has been completed based on these findings.

That is, the above problems have been solved by the following means.

<1> A producing method for a 3-difluoromethylpyrazole compound represented by Formula (1), the method comprising, in a reaction solvent containing at least one selected from Solvent group <I>, subjecting a compound represented by Formula (2), a hydrazine compound represented by Formula (3), and formaldehyde to a cyclocondensation reaction, and subsequently oxidizing the obtained pyrazole compound precursor.

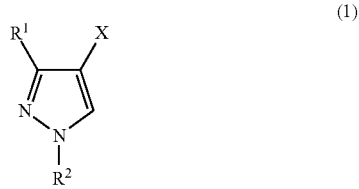

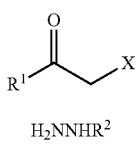

(2)

H₂NNHR² (3)

In the formulae, R¹ represents —CF₂H, R² represents a hydrogen atom, an alkyl group, an aryl group, or a heteroaryl group, and X represents —CN, —COOR³, or —CONR⁴R⁵, where R³ represents an alkyl group, and R⁴ and R⁵ represent a hydrogen atom or an alkyl group.

Solvent Group <I> an amide solvent, a urea solvent, a nitrile solvent, an ether solvent, a sulfoxide solvent, a sulfone solvent, an ester solvent, a hydrocarbon solvent, a halogen solvent, and a ketone solvent.

<2> The producing method according to <1>, in which the pyrazole compound precursor includes at least any of a compound represented by Formula (5) or a compound represented by Formula (6).

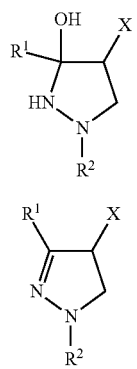

(5)

(6)

In the formulae, R¹, R², and X respectively have the same meanings as R¹, R², and X in Formula (1).

<3> The producing method according to <1> or <2>, in which the pyrazole compound precursor is oxidized using a persulfate under an acidic condition.

<4> The producing method according to any one of <1> to <3>, in which the pyrazole compound precursor is oxidized without isolating or purifying from a precursor solution obtained by the cyclocondensation reaction.

<5> The producing method according to any one of <1> to <4>, in which the cyclocondensation reaction is carried out in the absence of an acid catalyst and a base catalyst.

<6> A producing method for a 3-difluoromethylpyrazole-4-carboxylic acid compound represented by Formula (1A), the method comprising converting X in the 3-difluoromethylpyrazole compound obtained by the producing method according to any one of <1> to <5> to —COOH.

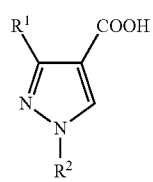

(1A)

In the formula, R¹ and R² respectively have the same meanings as R¹ and R² in Formula (1).

<7> A pyrazolidine compound represented by Formula (5).

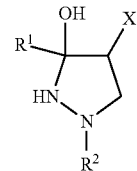

(5)

In the formula, R¹ represents —CF₂H, R² represents a hydrogen atom, an alkyl group, an aryl group, or a heteroaryl group, and X represents —CN, —COOR³, or —CONR⁴R⁵, where R³ represents an alkyl group, and R⁴ and R⁵ represent a hydrogen atom or an alkyl group.

<8> The pyrazolidine compound according to <7>, in which the R² is an alkyl group, and the X is —COOR³.

In the present invention, "%" used for indicating composition, purity, or amount used, and yield is based on the mass unless otherwise specified.

In the present invention, in a case where there are a plurality of substituents or linking groups represented by a specific symbol or formula (hereinafter, referred to as substituents or the like), or in a case where a plurality of substituents or the like are defined at the same time, the substituents or the like may be the same or different from each other, unless otherwise specified. The same applies to the definition of the number of substituents or the like. Further, in a case where a plurality of substituents or the like are close to each other (particularly in a case where they are adjacent to each other), they may be linked to each other to form a ring, unless otherwise specified. Further, unless otherwise specified, rings such as an alicyclic ring, an aromatic ring, and a heterocyclic ring may be condensed to form a fused ring.

In the present invention, in a case where there exists an R-form and an S-form based on an asymmetric carbon, any of them or a mixture thereof may be used unless otherwise specified.

In the present invention, the representation of a compound (including a complex) is used to mean not only the compound itself but also a salt thereof, and an ion thereof. In addition, it is meant to include those in which a part of the structure is changed within a range that does not impair the effects of the present invention. Furthermore, it is meant that a compound, which is not specified to be substituted or unsubstituted, may have any substituent within a range that does not impair the effects of the present invention. The same applies to the definitions of substituents or linking groups. In addition, in the present invention, for the description of the specific substituent, the description of a substituent T described later can be appropriately referred to.

In addition, in the present invention, the numerical range indicated by using "to" means a range including the numerical values before and after "to" as the lower limit value and the upper limit value, respectively.

In the producing methods for a 3-difluoromethylpyrazole compound and a 3-difluoromethylpyrazole-4-carboxylic acid compound according to the aspects of the present invention, the targeted 3-difluoromethylpyrazole compound and 3-difluoromethylpyrazole-4-carboxylic acid compound each can be produced in good yield with simple operation under mild conditions, while suppressing the generation of by-products, using relatively inexpensive and easily available compounds as raw materials. In addition, the pyrazolidine compound according to the aspect of the present invention is useful for producing a 3-difluoromethylpyrazole compound, as a synthetic intermediate in the producing method for a 3-difluoromethylpyrazole compound.

The above and other features and advantages of the present invention will be more obvious from the description below.

DESCRIPTION OF THE PREFERRED EMBODIMENTS

<<Producing Method of Embodiment of Present Invention>>

The producing method of the embodiment of the present invention includes both a producing method for a 3-difluoromethylpyrazole compound (hereinafter, sometimes referred to as a producing method for a carboxylic acid compound precursor) and a producing method for a 3-difluoromethylpyrazole-4-carboxylic acid compound (hereinafter, sometimes referred to as a producing method for a carboxylic acid compound).

In the producing method for a carboxylic acid compound precursor of the embodiment of the present invention, in a reaction solvent containing at least one selected from Solvent group <I>, a compound represented by Formula (2), a hydrazine compound represented by Formula (3), and formaldehyde represented by Formula (4) (three components) are subjected to a cyclocondensation reaction. Subsequently, the obtained pyrazole compound precursor is oxidized. By performing these reactions, a 3-difluoromethylpyrazole compound represented by Formula (1) can be produced.

The 3-difluoromethylpyrazole compound obtained in this manner can be converted into a predetermined carboxylic acid compound depending on the uses. That is, the producing method for a carboxylic acid compound of the embodiment of the present invention is a method in which X in the 3-difluoromethylpyrazole compound obtained by the producing method for a carboxylic acid compound precursor is converted to —COOH (details of the method will be described later, but for example a hydrolysis reaction). By this method, a 3-difluoromethylpyrazole-4-carboxylic acid compound represented by Formula (1A) can be produced.

The processes in the producing method of the embodiment of the present invention are shown below by a chemical equation. The symbols ($R^1$, $R^2$, and X) in the following chemical equation respectively have the same meanings as the symbols in the formulae described later.

Details of a reagent, a solvent, reaction conditions, and the like used in each process will be described later, but the present invention is not limited to the following description as long as the reaction of each process is not inhibited.

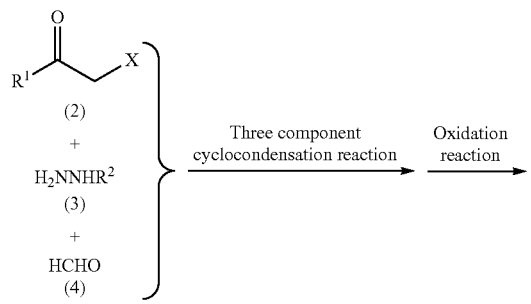

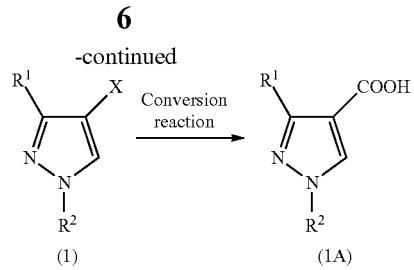

<Producing Method for 3-Difluoromethylpyrazole Compound>

(Cyclocondensation Reaction of a Compound Represented by Formula (2), a Hydrazine Compound Represented by Formula (3), and Formaldehyde)

In the present producing method, first, a compound (hereinafter, also referred to as a compound (2)) represented by Formula (2), a hydrazine compound (hereinafter, also referred to as a compound (3)) represented by Formula (3), and formaldehyde (hereinafter, also referred to as a compound (4)) are reacted in a reaction solvent containing at least one selected from Solvent group <I> described later (a three component cyclocondensation reaction is performed).

In the present invention, the performing of three component cyclocondensation reaction (in the present invention, also shortly referred to as cyclocondensation reaction) of the above-described compounds is not particularly limited in the reaction mode (reaction mechanism) as long as the targeted pyrazole compound precursor (details thereof will be described later) can be obtained; however, it is preferable, for example, to react each compound so as to undergo through a reaction mechanism described later, since it is possible to produce the carboxylic acid compound precursor while suppressing the generation of by-products such as isomers under mild conditions.

In the formulae, $R^1$ represents —$CF_2H$, $R^2$ represents a hydrogen atom, an alkyl group, an aryl group, or a heteroaryl group, and X represents —CN, —$COOR^3$, or —$CONR^4R^5$, where $R^3$ represents an alkyl group, and $R^4$ and $R^5$ represent a hydrogen atom or an alkyl group.

—Compound (2)—

The compound (2) is a compound represented by Formula (2) and containing a difluoroacetyl group.

In Formula (2), R' represents —$CF_2H$. In a case where R' is a —$CF_2H$ group, in the producing method of the embodiment of the present invention, the targeted compound can be produced in good yield even under mild reaction conditions while suppressing the generation of by-products such as isomers.

X may be any functional group that can be converted into a carboxy group in the producing method for a carboxylic acid compound of the embodiment of the present invention, is appropriately determined depending on the conversion reaction, and a hydrolyzable group that forms a carboxy group by a hydrolysis reaction is usually selected. In the present invention, X is —CN, —$COOR^3$, or —$CONR^4R^5$, and from the viewpoint of easy availability, —$COOR^3$ is preferred, and —$COOC_2H_5$ is more preferred. Here, $R^3$ is an alkyl group, and $R^4$ and $R^5$ are each a hydrogen atom or an alkyl group. The alkyl group that can be adopted as $R^3$ to $R^5$ is not particularly limited and may be a linear, branched, or cyclic alkyl group, and the carbon number thereof is preferably 1 to 20, more preferably 1 to 12, and still more preferably 1 to 6. Examples of the alkyl group include methyl, ethyl, propyl, butyl, and hexyl. Among them, as the alkyl group that is used as $R^3$, ethyl is particularly preferred.

In the present invention, the compound (2) is preferably an alkyl ester of difluoroacetoacetic acid.

—Compound (3)—

The compound (3) is a compound represented by Formula (3).

In Formula (3), $R^2$ is a hydrogen atom, an alkyl group, an aryl group, or a heteroaryl group, preferably an alkyl group, and more preferably methyl.

The alkyl group that can be adopted as $R^2$ has the same meaning as the alkyl group that can be adopted as $R^3$ to $R^5$, and the preferred ones are also the same. However, a particularly preferred alkyl group that can be adopted as $R^2$ is methyl.

The aryl group that can be adopted as $R^2$ is not particularly limited, and the carbon number thereof is preferably 6 to 30, more preferably 6 to 22, and still more preferably 6 to 18. Examples of the aryl group include phenyl and 1-naphthyl.

The heteroaryl group that can be adopted as $R^2$ is a monocyclic group consisting of a 5-membered or 6-membered ring having at least one hetero atom (for example, an oxygen atom, a sulfur atom, or a nitrogen atom) as a ring-constituting atom and having 1 to 20 carbon atoms or a group consisting of a fused ring containing this monocyclic ring. An example of the heteroaryl group includes an aromatic heterocyclic group among the heterocyclic groups in the substituent T described later.

—Compound (4)—

The compound (4) is formaldehyde, and any form of formaldehyde can be used. For example, an aqueous solution of formaldehyde (formalin) can be preferably used. The concentration of formaldehyde in formal in is not particularly limited and can be set appropriately. Formalin may contain about 10% of methanol as a stabilizer.

Any one of the compounds (2) to (4) used in the producing method of the embodiment of the present invention may be appropriately synthesized or may be a commercially available product. In particular, all of these compounds are available at a relatively low price, and the use of these compounds as raw materials contributes to the reduction of production cost.

—Reaction Solvent Containing At Least One Selected from Solvent Group <I>—

The above cyclocondensation reaction is performed in a reaction solvent containing at least one solvent selected from Solvent group <I>. In the present invention, performing the cyclocondensation reaction in the reaction solvent means reacting the compounds (2) to (4) in a state of being dissolved or dispersed in the reaction solvent. In a case where the cyclocondensation reaction is performed in such a reaction solvent, the targeted compound can be produced in good yield even under mild reaction conditions while suppressing the generation of by-products such as isomers.

Each solvent contained in Solvent group <1> listed below may be one that dissolves or disperses the above compounds and is preferably a solvent (for example, an aprotonic solvent) inert (difficult to promote or give rise to decomposition of a pyrazole compound precursor) to a pyrazole compound precursor described later.

Solvent Group <I> an amide solvent, a urea solvent, a nitrile solvent, an ether solvent, a sulfoxide solvent, a sulfone solvent, an ester solvent, a hydrocarbon solvent, a halogen solvent, and a ketone solvent.

The amide solvent may be a solvent of a compound having an amide bond, and examples thereof include dimethylformamide, dimethylacetamide, N-methyl-2-pyrrolidinone, and N-ethyl-2-pyrrolidinone. The urea solvent may be a solvent of a compound having a urea bond, and examples thereof include 1,3-dimethyl-2-imidazolidinone. The nitrile solvent may be a solvent of a compound having a nitrile group, and examples thereof include acetonitrile, propionitrile, and benzonitrile. The ether solvent may be a solvent of a compound having an ether bond, and examples thereof include diethyl ether, tert-butyl methyl ether, diisopropyl ether, tetrahydrofuran, dimethoxyethane, ethylene glycol dimethyl ether, diethylene glycol dimethyl ether (diglyme), and dioxane. The sulfoxide solvent may be a solvent of a compound having a sulfinyl bond (—S(=O)—), and examples thereof include dimethyl sulfoxide. The sulfone solvent may be a solvent of a compound having a sulfonyl bond (—S(=O)$_2$—), and examples thereof include sulfolane. The ester solvent may be a solvent of a compound having an ester bond, and examples thereof include carboxylic acid alkyl ester solvents such as ethyl acetate, isopropyl acetate, and butyl acetate. The ketone solvent may be a solvent of a compound having an independent carbonyl group (which does not form an amide bond, a urea bond, or an ester bond), and examples thereof include ketone solvents such as acetone, methyl ethyl ketone, and cyclohexanone.

The hydrocarbon solvent may be a solvent consisting of a hydrocarbon and includes an aliphatic hydrocarbon solvent and an aromatic hydrocarbon solvent. The aliphatic hydrocarbon solvent is not particularly limited, and examples thereof include hexane, heptane, and cyclohexane. The aromatic hydrocarbon solvent is not particularly limited, and examples thereof include toluene, ethylbenzene, and xylene.

The halogen solvent refers to a solvent consisting of a compound having a halogen atom (preferably each atom of fluorine, chlorine, and bromine) in the molecule and is classified as a halogen solvent even in a case where the compound having a halogen atom has any of the abovementioned bonds in the molecule. The halogen solvent is not particularly limited, and examples thereof include an aliphatic halogen solvent such as methylene chloride, chloroform, and ethylene dichloride, and an aromatic halogen solvent such as chlorobenzene.

The solvent selected from Solvent group <I> is preferably at least one selected from an amide solvent, a urea solvent, a nitrile solvent, an ether solvent, a sulfoxide solvent, a sulfone solvent, or an ester solvent and more preferably at least one selected from an amide solvent or an ether solvent from the viewpoint of easily obtaining a uniformly mixed reaction system or the yield of the compound (1), and still more preferably an ether solvent and particularly preferably a dimethoxyethane solvent or diglyme solvent from the viewpoint of yield and selectivity of the compound (1).

The reaction solvent may contain one of the solvents selected from Solvent group <1> and may contain two or more thereof.

The reaction solvent may contain a solvent other than the solvent included in Solvent group <I>, within the range that does not affect the reaction in which the compound (1) is added, particularly the cyclocondensation reaction or the decomposition promotion of a compound represented Formula (6) (hereinafter, also referred to as a compound (6)) described later.

Examples of the solvent other than the solvent included in Solvent group <1> include a protonic solvent and water. Examples of the protonic solvent include an alcohol solvent and specifically include methanol, ethanol, and isopropanol, and ethanol is preferred. The alcohol solvent and water may be respectively the alcohol (stabilizer) and water derived from formalin.

In the producing method of the embodiment of the present invention, the compound represented Formula (1) can be obtained in a case where an alcohol solvent is used as a reaction solvent. However, the alcohol solvent is used in combination with the solvent of Solvent group <I> described above, since the alcohol solvent may promote the decomposition of the compound (6), which is described later (or, as a result of accelerating the reaction from a compound represented by Formula (5) (hereinafter, also referred to as a compound (5)) described later to the compound (6) described later, a side reaction via the compound (6) becomes remarkable). In this case, from the viewpoint of selectivity, the use in combination with an ether solvent is preferred, and the use in combination with a diglyme is more preferred.

In a case where the reaction solvent contains a solvent other than the solvent included in Solvent group <I>, the content rate of the solvent included in Solvent group <I> in the total amount of the reaction solvent is preferably 25% by mass or more, more preferably 50% by mass or more, still more preferably 75% by mass or more, particularly preferably 90% by mass or more, and most preferably 95% by mass or more, and further the reaction solvent can be a solvent included in Solvent group <I>. On the other hand, in a case where the alcohol solvent is contained, the content rate of the alcohol solvent in the total amount of the reaction solvent is preferably 75% by mass or less, more preferably 50% by mass or less, and still more preferably 25% by mass or less. In a case where the alcohol solvent and the ether solvent are used in combination, the ratio of the content rate of the alcohol solvent (preferably ethanol) to the content rate of the ether solvent is not particularly limited, but in terms of selectivity, the ratio is, for example, preferably 25:75 to 75:25 and more preferably 40:60 to 60:40.

(Reaction Condition for Cyclocondensation Reaction, and the Like)

—Mixing Method—

The mixing method (the order of charging but not the order of reaction) each compound in the cyclocondensation reaction is not particularly limited. Examples of the mixing method include, a method of mixing (dropwise adding) the mixture of the compound (2) and the reaction solvent (a solution of the compound (2)) sequentially with the compound (3) and the compound (4), a method of mixing (dropwise adding) the mixture of the compound (3) and the reaction solvent (a solution of the compound (3)) sequentially with the compound (4) and the compound (2), and a method of mixing (dropwise adding) the mixture of the compound (4) and the reaction solvent (a solution of the compound (4)) sequentially with the compound (3) and the compound (2). In the mixing method, the compound to be mixed may be a mixture (solution) with various solvents (preferably the above reaction solvent) or the compound may be mixed directly without being diluted.

—Mixing Amount—

The mixing amount (charging ratio) of each compound in the cyclocondensation reaction is not particularly limited, but it is preferable to react each of the compound (3) and the compound (4) in a ratio of 0.5 to 2.0 mol and more preferably in a ratio of 0.8 to 1.2 mol with respect to 1 mol of the compound (2), in terms of simplifying the purification operation and reducing the production cost without impairing the yield and the selectivity.

The amount of the reaction solvent used is not particularly limited but is preferably 0.5 to 50 times (mass basis) and more preferably 1 to 20 times (mass basis) the compound (2).

—Reaction Temperature and Reaction Time—

The reaction temperature of the cyclocondensation reaction is not particularly limited as long as the targeted reaction proceeds; however, the reaction temperature is usually set in the temperature range between the melting point or higher and the boiling point or lower of the reaction solvent. From the viewpoint of preventing the reaction efficiency from decreasing under mild conditions and suppressing the side reaction, the reaction temperature is preferably $-30°$ C. to $120°$ C. and more preferably $0°$ C. to $80°$ C.

Since the reaction time of the cyclocondensation reaction is set depending on the reaction temperature, the reaction solvent, the kind of the catalyst, the amount of catalyst used, or the like, which will be described later, the reaction time is not uniquely determined; however, from the viewpoint of productivity, the reaction time is preferably 0.1 to 24 hours and more preferably 0.5 to 6 hours.

—Acid Catalyst or Base Catalyst—

In the present invention, the cyclocondensation reaction can be carried out in the absence of an acid catalyst and/or a base catalyst.

As the acid that can serve as an acid catalyst, an organic acid such as acetic acid, inorganic acids such as hydrochloric acid and sulfuric acid, and Lewis acids such as titanium tetrachloride and a boron trifluoride-diethyl ether complex are mentioned. The base that can serve as a base catalyst may be any base that does not undergo the cyclocondensation reaction (the compound (3) is not a base catalyst), and an example thereof includes at least one selected from the group consisting of an inorganic base, an organic base, and a metal alkoxide.

The inorganic base is not particularly limited, examples thereof include ammonia, an alkali metal hydroxide, an alkali metal carbonate, an alkali metal hydrogen carbonate, and an alkali metal hydrogen phosphates. Specifically, lithium hydroxide, sodium hydroxide, potassium hydroxide, lithium carbonate, sodium carbonate, potassium carbonate, sodium hydrogen carbonate, potassium hydrogen carbonate, disodium hydrogen phosphate, sodium dihydrogen phosphate, dipotassium hydrogen phosphate, or potassium dihydrogen phosphate is preferred and sodium hydroxide, sodium carbonate, sodium hydrogen carbonate, disodium hydrogen phosphate, or sodium dihydrogen phosphate is more preferred.

The organic base is not particularly limited, and examples thereof include an aromatic amine and an aliphatic amine. Specifically, pyridine, lutidine, collidine, triethylamine, diethylamine, N,N-diisopropylethylamine, N,N-diisopropylpentylamine, morpholine, piperidine, and pyrrolidine are mentioned, and pyridine, triethylamine or piperidine is preferred.

The metal alkoxide is not particularly limited, but preferably includes sodium methoxide, potassium methoxide, sodium ethoxide, potassium ethoxide, sodium tert-butoxide, and potassium t-butoxide, and sodium methoxide or sodium ethoxide is more preferred.

In a case where the acid catalyst or base catalyst is made to coexist, the amount of each catalyst used is preferably 0.01 to 5 mol and more preferably 0.1 to 2 mol with respect to 1 mol of the compound (2).

In the present invention, since the compound (1) can be synthesized with higher yield and higher selectivity, it is preferable to perform the cyclocondensation reaction in the absence of the acid catalyst and the base catalyst. In the present invention, "the acid catalyst and the base catalyst do not coexist" includes an aspect in which the acid catalyst and the base catalyst each coexist in a proportion of less than 0.01 mol with respect to 1 mol of the compound (2), in addition to the aspect in which neither the acid catalyst nor the base catalyst is used.

—Other—

In the above cyclocondensation reaction, the inside of the reaction vessel may be replaced with an inert gas such as nitrogen and argon.

The cyclocondensation reaction in the producing method of the embodiment of the present invention is one of the multi-component reactions, and the three components of the compounds (2) to (4) are subjected to the addition (condensation) reaction and then the intramolecular cyclization reaction to form a pyrazole compound precursor.

The details of the reaction mechanism of these reactions are not clear yet, but a serial reaction mechanism via compound (5) shown in the following scheme is conceivable. In the following reaction mechanism, the generation mechanism of positional isomers described later is also shown. The reaction mechanism is shown for the aspect adopting —COOR$^3$ as X in Formula (1) or the like, R$^1$ and R$^2$ respectively have the same meanings as R$^1$ and R$^2$ in Formula (1). In addition, only the compound (5) and the compound (6) are shown as the pyrazole compound precursor, but compounds other than these may be included as described later.

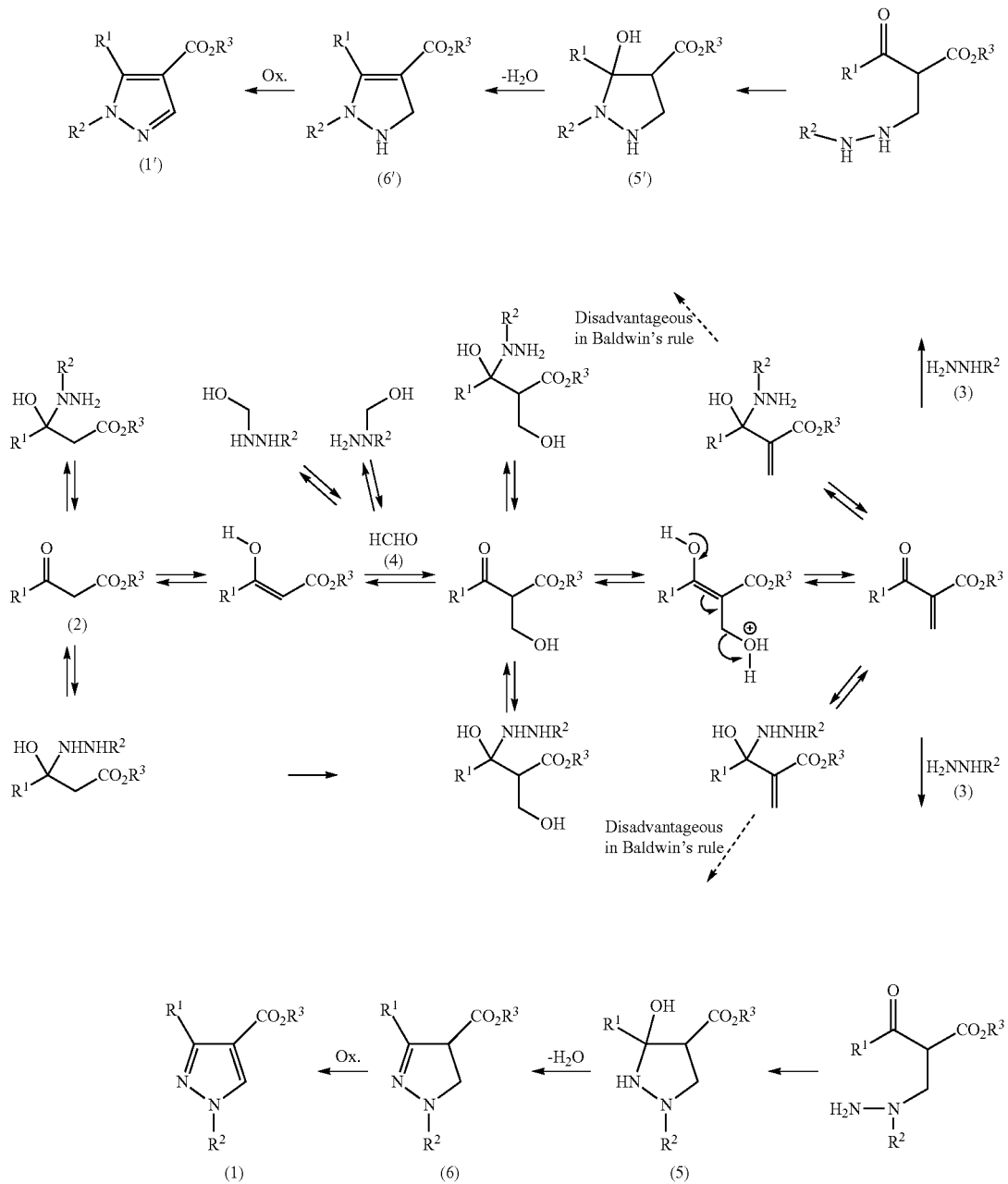

(Pyrazole Compound Precursor)

The pyrazole compound precursor obtained by the above cyclocondensation reaction is not limited to the compound (5) and the compound (6) described in the above reaction mechanism and may be any compound that can generate a 3-difluoromethylpyrazole-4-carboxylic acid compound by the subsequent oxidation reaction. For example, as shown in the above reaction mechanism, it is preferable that at least one of the compound (5) or the compound (6) (hereinafter, also referred to as intermediate M) is included.

It is presumed that the compound (6) is generated as a result of the procession of the dehydration reaction of the compound (5), which is firstly generated, under the reaction conditions of the above-described cyclocondensation reaction. The conversion rate of the compound (5) to the compound (6) depends on the reaction solvent used, the presence or absence of the acid catalyst or the base catalyst, and the like.

In the above reaction mechanism, the conversion rate of the compound (5) to the compound (6) can be improved by using the acid catalyst; however, the side reaction tends to be accelerated. Accordingly, in a case where the generation of the compound (5) is completed, the conversion to the compound (6) may not necessarily have to be performed, and the oxidation reaction may be performed while generating the compound (6) in the oxidation process described later. In a case where the conversion of the compound (5) to the compound (6) is not performed (can be suppressed), the decomposition of the generated compound (6) is suppressed, and the compound (1) can be synthesized with higher yield and higher selectivity. In the present invention, that the compound (1) can be synthesized with higher selectivity means that the compound (1) can be synthesized as a main component by suppressing the generation of positional isomers of the compound (1) (in particular, a compound (1') which is a positional isomer of the substituent $R^2$ derived from the hydrazine compound). The selectivity in this case can be evaluated by, for example, the proportion (isomer ratio) of the generation amount (mass basis) of the compound (1) with respect to the generation amount (mass basis) of the positional isomer of the compound (1).

In addition to the intermediate M (at least any one of the compound (5) or the compound (6)), the pyrazole compound precursor obtained by the above cyclocondensation reaction may include positional isomers of the compound (5) or the compound (6), which are compounds represented by Formula (5') or compounds represented by Formula (6'), as shown in the following scheme.

In addition, in a case where a nucleophilic solvent, for example, an alcohol solvent and a carboxylic acid solvent, is used in the above cyclocondensation reaction or the subsequent oxidation reaction, it is also considered that a compound represented by Formula (7) obtained by reacting the compound (6) with the nucleophilic solvent is contained.

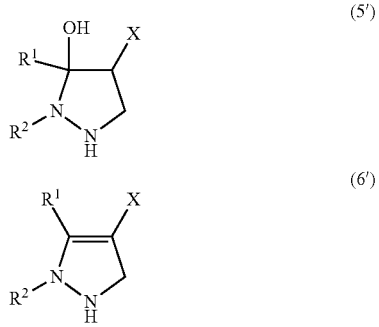

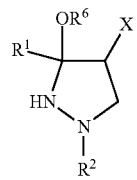

In the formulae, $R^1$, $R^2$, and X respectively have the same meanings as $R^1$, $R^2$, and X in Formula (1).

$R^6$ is a residue of the nucleophilic solvent such as an alcohol and a carboxylic acid reacted with the compound (6) and specifically represents alkyl, alkylcarbonyl, or arylcarbonyl.

As described above, the targeted pyrazole compound precursor can be obtained by performing the cyclocondensation reaction.

(Oxidation Reaction of Pyrazole Compound Precursor)

In the producing method of the embodiment of the present invention, the pyrazole compound precursor obtained by the above cyclocondensation reaction is subsequently oxidized to synthesize a 3-difluoromethylpyrazole compound represented by Formula (1).

This oxidation reaction can be carried out under acidic conditions using a known oxidizing agent, and preferably, as shown in the following chemical equation, a pyrazole compound precursor including the intermediate M (at least one of the compound (5) or the compound (6)) is oxidized using a known oxidizing agent.

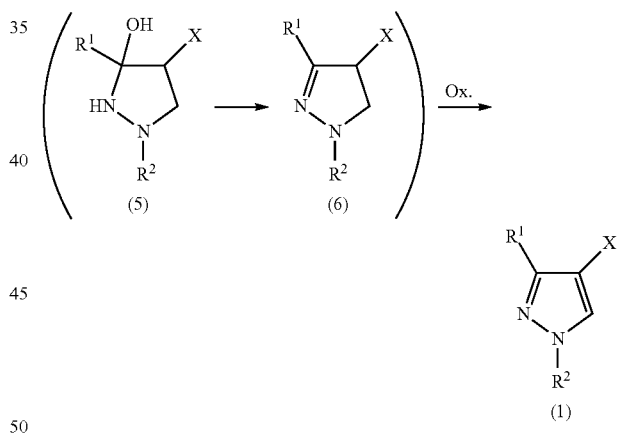

—Oxidizing Agent and Acid—

The oxidation reaction can be usually performed by treating the pyrazole compound precursor with an oxidizing agent in the presence of an acid and a solvent.

The oxidizing agent is not particularly limited, but examples of the preferred oxidizing agent include hydrogen peroxide, persulfates such as potassium persulfate and sodium persulfate (including peroxymonosulfate and peroxydisulfate), potassium hydrogen persulfate, 2,3-dichloro-5,6-dicyano-1,4-benzoquinone, tetrachloro-1,4-benzoquinone, palladium carbon, manganese dioxide, potassium permanganate, and oxygen gas. These oxidizing agents may be used alone or in a combination of two or more thereof. The oxidizing agent is preferably used in an amount of 0.5 to 10 mol and more preferably 1 to 3 mol, with respect to 1 mol of the compound (2).

The acid is not particularly limited, and examples thereof include inorganic acids such as sulfuric acid, hydrochloric acid, and phosphoric acid, and organic acids such as acetic acid. The acid is preferably used in an amount of 0.5 to 10 mol and more preferably 1 to 3 mol, with respect to 1 mol of the compound (2).

The oxidizing agent and the acid may be used as a solution mixed with the following reaction solvent.

In the present invention, an oxidation reaction using a persulfate (particularly peroxydisulfate) as an oxidizing agent is preferred under the acidic conditions provided by the presence of the above acid.

—Reaction Solvent—

The solvent used in the oxidation reaction is not particularly limited, and examples thereof include, an amide solvent, a urea solvent, a nitrile solvent, an ether solvent, a sulfoxide solvent, a sulfone solvent, an ester solvent, a hydrocarbon solvent, a halogen solvent, a ketone solvent, an alcohol solvent, a carboxylic acid solvent, and water.

The amide solvent, the urea solvent, the nitrile solvent, the ether solvent, the sulfoxide solvent, the sulfone solvent, the ester solvent, the hydrocarbon solvent, the halogen solvent, and the ketone solvent are the same as the solvents included Solvent group <I> used in the cyclocondensation reaction. Further, the alcohol solvent has the same meaning as an alcohol solvent other than the solvent included in Solvent group <I>. The carboxylic acid solvent may be a solvent consisting of a compound having —COOH, and examples thereof include acetic acid and trifluoroacetic acid.

These solvents may be used alone or in a combination of two or more thereof.

—Reaction Condition for Oxidation Reaction—

The reaction temperature is not particularly limited as long as the oxidation reaction of the pyrazole compound precursor proceeds and is preferably 0° C. to 120° C. and more preferably 30° C. to 80° C., as a relatively mild reaction temperature. Since the reaction time is set depending on the reaction conditions, the reaction time is not uniquely determined; however, from the viewpoint of productivity, the reaction time is preferably 0.1 to 12 hours and more preferably 0.2 to 3 hours.

In a case where a post-treatment is required after the completion of the oxidation reaction, a usual post-treatment can be adopted depending on the oxidizing agent used. In this case, the conversion reaction described later can be carried out simultaneously.

In the producing method of the embodiment of the present invention, the pyrazole compound precursor (preferably the intermediate M) can be directly used in the next process without isolation or purification from the precursor solution obtained by the cyclocondensation reaction. In this case, the acid and the oxidizing agent may be added as they are to the solution of the pyrazole compound precursor (preferably the intermediate M), or the acid and the oxidizing agent may be added after adding a new solvent to the solution or replacing the solution with a new solution.

That is, in the producing method of the embodiment of the present invention, the pyrazole compound precursor may be isolated or purified by a usual method described below and subjected to the oxidation reaction; however, from the viewpoint of production efficiency and yield, it is preferable that the pyrazole compound precursor is oxidized without being isolated or purified from the precursor solution obtained by the cyclocondensation reaction.

In the present invention, "the pyrazole compound precursor is oxidized without being isolated or purified from the precursor solution obtained by the cyclocondensation reaction" means that the cyclocondensation reaction and the oxidation reaction are consecutively performed without intervening the process of isolating or purifying the pyrazole compound precursor from the precursor solution. Here, "consecutively performed" means that the cyclocondensation reaction and the oxidation reaction are temporally performed and includes an aspect in which another process (for example, a concentration adjustment process) is performed between the cyclocondensation reaction and the oxidation reaction. In addition, the aspect in which the cyclocondensation reaction and the oxidation reaction are consecutively performed also includes an aspect in which the time, place, or performer is appropriately changed.

In the present invention, the aspect consecutively performed is preferably an aspect performed in one-pot mode (one-pot reaction). The one-pot reaction usually means consecutively performing a multi-step reaction in which each of raw materials is sequentially charged into the same reaction vessel (pot) without isolating or purifying the target product of each reaction from each reaction solution; however, in the present invention, the one-pot reaction may be a reaction mode in which the targeted product of each reaction is not isolated or purified from each reaction solution and is not necessarily limited to an aspect in which the reaction is performed in the same and one reaction vessel.

By performing the oxidation reaction as described above, the targeted 3-difluoromethylpyrazole compound represented by Formula (1) can be produced.

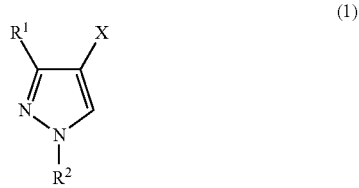

In Formula (1), $R^1$, X, and $R^2$ respectively have the same meanings as IV and X in Formula (2) and $R^2$ in Formula (3), and the preferred ones are also the same.

The 3-difluoromethylpyrazole compound can also be isolated or purified by a usual method described later.

<Producing Method for 3-Difluoromethylpyrazole-4-Carboxylic Acid Compound>

In the producing method for a carboxylic acid compound, a 3-difluoromethylpyrazole-4-carboxylic acid compound represented by Formula (1A) can be produced by converting X in the 3-difluoromethylpyrazole compound represented by Formula (1), obtained by the producing method of the carboxylic acid compound precursor, to —COOH.

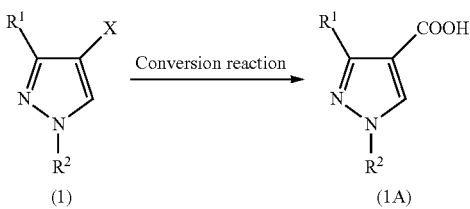

In the formulae, $R^1$, $R^2$, and X respectively have the same meanings as $R^1$, $R^2$, and X in Formula (1).

As a method of converting X to —COOH, a usual conversion method can be applied without particular limitation, and examples thereof include a hydrolysis reaction. This hydrolysis reaction can be carried out under appropriate reaction conditions or the like, depending on each of the groups that can be adopted as X.

In the present invention, the conversion reaction may be carried out together with the isolation treatment or the purification treatment.

The conversion reaction can be carried out without isolating or purifying the 3-difluoromethylpyrazole compound from the reaction solution obtained by the oxidation reaction.

The method for isolating the compound represented by Formula (1A) obtained by the producing method of the embodiment of the present invention is not particularly limited, and the compound represented by Formula (1A) can be isolated and purified by a usual method such as extraction, crystallization, distillation, or column chromatography.

By performing the conversion reaction as described above, the targeted 3-difluoromethylpyrazole-4-carboxylic acid compound represented by Formula (1A) can be produced. As described later, this 3-difluoromethylpyrazole-4-carboxylic acid compound is a compound useful as a pharmaceutical agent and an agricultural chemical, and synthetic intermediates thereof.

In any one of the producing methods of the embodiment of the present invention, as described above, a targeted compound can be produced in good yield and high selectivity with simple operation under mild conditions, using a relatively inexpensive and easily available reagent as raw materials.

<<Pyrazolidine Compound Represented by Formula (5)>>

By the above-described producing method of the embodiment of the present invention, a pyrazolidine compound represented by Formula (5) is synthesized as a synthetic intermediate as one kind of the pyrazole compound precursors. This compound (5) is subjected to the oxidation reaction in the producing method of the embodiment of the present invention and further to the above-described conversion reaction to provide a 3-difluoromethylpyrazole compound represented by Formula (1) and a 3-difluoromethylpyrazole-4-carboxylic acid compound represented by Formula (1A), and is a useful synthetic intermediate for these compounds.

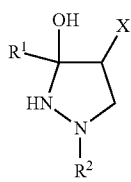

(5)

In the formulae, $R^1$ represents $R^2$ represents a hydrogen atom, an alkyl group, an aryl group, or a heteroaryl group, and X represents —CN, —COOR$^3$, or —CONR$^4R^5$, where $R^3$ represents an alkyl group, and $R^4$ and $R^5$ represent a hydrogen atom or an alkyl group. R' to $R^5$ and X in Formula (5) respectively have the same meaning as $R^1$ to $R^5$ and X in Formula (1), and the preferred ones are also the same.

<Substituent T>

Examples of the substituent T include the followings.

An alkyl group (preferably an alkyl group having 1 to 20 carbon atoms, for example, methyl, ethyl, isopropyl, t-butyl, pentyl, heptyl, 1-ethylpentyl, benzyl, 2-ethoxyethyl, and 1-carboxymethyl), an alkenyl group (preferably an alkenyl group having 2 to 20 carbon atoms, for example, vinyl, allyl, and oleyl), an alkynyl group (preferably an alkynyl group having 2 to 20 carbon atoms, for example, ethynyl, butadiynyl, and phenylethynyl), a cycloalkyl group (preferably a cycloalkyl group having 3 to 20 carbon atoms, for example, cyclopropyl, cyclopentyl, cyclohexyl, and 4-methylcyclohexyl), an aryl group (preferably an aryl group having 6 to 26 carbon atoms, for example, phenyl, 1-naphthyl, 4-methoxyphenyl, 2-chlorophenyl, and 3-methylphenyl), a heterocyclic group (preferably a 5-membered or 6-membered heterocyclic group having 1 to 20 carbon atoms and having at least one oxygen atom, sulfur atom, or nitrogen atom is more preferred. The heterocyclic group includes an aromatic heterocyclic group and an aliphatic heterocyclic group, for example, tetrahydropyranyl, tetrahydrofuranyl, 2-pyridyl, 4-pyridyl, 2-imidazolyl, 2-benzimidazolyl, 2-thiazolyl, and 2-oxazolyl), an alkoxy group (preferably an alkoxy group having 1 to 20 carbon atoms, for example, methoxy, ethoxy, isopropyloxy, and benzyloxy), an aryloxy group (preferably an aryloxy group having 6 to 26 carbon atoms, for example, phenoxy, 1-naphthyloxy, 3-methylphenoxy, and 4-methoxyphenoxy), a heterocyclic oxy group (a group in which —O— group is bonded to the above heterocyclic group), an alkoxycarbonyl group (preferably an alkoxycarbonyl group having 2 to 20 carbon atoms, for example, ethoxycarbonyl and 2-ethylhexyloxycarbonyl), an aryloxycarbonyl group (preferably an aryloxycarbonyl group having 6 to 26 carbon atoms, for example, phenoxycarbonyl, 1-naphthyloxycarbonyl, 3-methylphenoxycarbonyl, and 4-methoxyphenoxycarbonyl), a heterocyclic oxycarbonyl group (a group in which an —O—CO— group is bonded to the above heterocyclic group), an amino group (preferably including an amino group having 0 to 20 carbon atoms, an alkylamino group, or an arylamino group, for example, amino, N,N-dimethylamino, N,N-diethylamino, N-ethylamino, and anilino), a sulfamoyl group (preferably a sulfamoyl group having 0 to 20 carbon atoms, for example, N,N-dimethylsulfamoyl and N-phenylsulfamoyl), an acyl group (a group including an alkylcarbonyl group, an alkenylcarbonyl group, an alkynylcarbonyl group, an arylcarbonyl group, and a heterocyclic carbonyl group and preferably an acyl group having 1 to 20 carbon atoms, for example, acetyl, propionyl, butyryl, octanoyl, hexadecanoyl, acryloyl, methacryloyl, crotonoyl, benzoyl, naphthoyl, and nicotinoyl), an acyloxy group (a group including an alkylcarbonyloxy group, an alkenylcarbonyloxy group, an alkynylcarbonyloxy group, an arylcarbonyloxy group, and a heterocyclic carbonyloxy group and preferably an acyloxy group having 1 to 20 carbon atoms, for example, acetyloxy, propionyloxy, butyryloxy, octanoyloxy, hexadecanoyloxy, acryloyloxy, methacryloyloxy, crotonoyloxy, benzoyloxy, naphthoyloxy, and nicotinoyloxy), an aryloyloxy group (preferably an aryloyloxy group having 7 to 23 carbon atoms, for example, benzoyloxy), a carbamoyl group (preferably a carbamoyl group having 1 to 20 carbon atoms, for example, N,N-dimethylcarbamoyl and N-phenylcarbamoyl), an acylamino group (preferably an acylamino group having 1 to 20 carbon atoms, for example, acetylamino and benzoylamino), an alkylthio group (preferably an alkylthio group having 1 to 20 carbon atoms, for example, methylthio, ethylthio, isopropylthio, and benzylthio), an arylthio group (preferably an arylthio group having 6 to 26 carbon atoms, for example, phenylthio, 1-naphthylthio, 3-methylphenylthio, and 4-methoxyphenylthio), a heterocyclic thio group (a group in which a —S— group is bonded to the above heterocyclic group), an alkylsulfonyl group (preferably an alkylsulfonyl group having 1 to 20 carbon atoms, for example, methylsulfonyl and ethylsulfonyl), an arylsulfonyl group (preferably an arylsulfonyl group having 6 to 22 carbon atoms, for example, benzenesulfonyl), an alkylsilyl group (preferably an alkylsilyl group having 1 to 20 carbon atoms, for example, monomethylsilyl, dimethylsilyl, trimethylsilyl, and triethylsilyl), an arylsilyl group (preferably an arylsilyl group having 6 to 42 carbon atoms, for example, triphenylsilyl), a phosphoryl group (preferably a phosphate group having 0 to 20 carbon atoms), for example, —OP(=O)($R^P$)$_2$), a phosphonyl group (preferably a phosphonyl group having 0 to 20 carbon atoms, for example, —P(=O)($R^P$)$_2$), a phosphinyl group (preferably a phosphinyl group having 0 to 20 carbon atoms, for example, —P($R^P$)$_2$), a sulfo group (a sulfonic acid group), a hydroxy group, a sulfanyl group, a cyano group, a halogen atom (for example, a fluorine atom, a chlorine atom, a bromine atom, and an iodine atom), and the like are mentioned.

$R^P$ is a hydrogen atom, a hydroxy group, or a substituent other than a hydroxy group. As the substituent, the above-described substituent T is mentioned, but the substituent is preferably an alkyl group (preferably having 1 to 24 carbon atoms, more preferably 1 to 12 carbon atoms, still more preferably 1 to 6 carbon atoms, and particularly preferably 1 to 3 carbon atoms), an alkenyl group (preferably having 2 to 24 carbon atoms, more preferably 2 to 12 carbon atoms, still more preferably 2 to 6 carbon atoms, and particularly preferably 2 to 3 carbon atoms), an alkynyl group (preferably having 2 to 24 carbon atoms, more preferably 2 to 12 carbon atoms, still more preferably 2 to 6 carbon atoms, and particularly preferably 2 to 3 carbon atoms), an aralkyl group (preferably having 7 to 22 carbon atoms, more preferably 7 to 14 carbon atoms, and particularly preferably 7 to 10 carbon atoms), an aryl group (preferably having 6 to 22 carbon atoms, more preferably 6 to 14 carbon atoms, and particularly preferably 6 to 10 carbon atoms), an alkoxy group (preferably having 1 to 24 carbon atoms, more preferably 1 to 12 carbon atoms, still more preferably 1 to 6 carbon atoms, and particularly preferably 1 to 3 carbon atoms), an alkenyloxy group (preferably having 2 to 24 carbon atoms, more preferably 2 to 12, still more preferably 2 to 6, and particularly preferably 2 to 3 carbon atoms), an alkynyloxy group (preferably having 2 to 24 carbon atoms, more preferably 2 to 12, still more preferably 2 to 6 carbon atoms, and particularly preferably 2 to 3 carbon atoms), an aralkyloxy group (preferably having 7 to 22 carbon atoms, more preferably 7 to 14, and particularly preferably 7 to 10 carbon atoms), and aryloxy group (preferably having 6 to 22 carbon atoms, more preferably 6 to 14 carbon atoms, and particularly preferably 6 to 10 carbon atoms).

In addition, in each group of these groups mentioned as the substituent T, the substituent T described above may be further substituted.

In a case where a compound, a substituent, a linking group, and the like include an alkyl group, an alkylene group, an alkenyl group, an alkenylene group, an alkynyl group, and/or an alkynylene group, these groups may be cyclic or linear, or linear or branched. These groups may be substituted as described above or not substituted.

EXAMPLES

Hereinafter, the present invention will be described in more detail with reference to Examples. It is noted that the present invention is not limited to this. In the present invention, room temperature means 20° C. to 25° C.

Example 4

(Synthesis of Compound Represented by Formula (1))
—Cyclocondensation Reaction—

A solution in which a 37% aqueous formalin (the compound (4), 164.3 mg) solution and diglyme (0.3 mL) were mixed and a solution of ethyl 4,4-difluoroacetoacetate (the compound (2), 337.2 mg) in a diglyme (0.3 mL) solution were added dropwise in order to a diethylene glycol dimethyl ether (hereinafter, referred to as diglyme) solution (1.7 mL) of methylhydrazine (the compound (3), 94.6 mg, the molar equivalent ratio to the compound (2) is shown in Table 1) at 5° C. The mixture solution was then stirred at 50° C. for 2 hours. In this manner, the cyclocondensation reaction was performed to obtain a precursor solution.

—Oxidation Reaction—

Next, a solution obtained by mixing potassium persulfate (potassium peroxydisulfate, 0.81 g) and concentrated sulfuric acid (0.39 g) in dimethylformamide (8.3 mL) were added in the same vessel without isolating and purifying the reaction mixture from the obtained precursor solution, and the resultant mixture was further stirred at 50° C. for 30 minutes to carry out an oxidation reaction.

The obtained reaction solution was cooled to room temperature, transferred to a volumetric flask, and diluted with ethyl acetate such that the total volume was 50 mL.

—Confirmation of Compound Represented by Formula (1)—

10 mL of the supernatant of the solution diluted above was washed with each of 10 mL of 1N hydrochloric acid water, 10 mL of saturated sodium hydrogen carbonate solution, and 10 mL of saturated saline, and the organic phase was concentrated in the reduced pressure environment. The concentrated residue was purified by column chromatography (eluent: ethyl acetate/hexane=1/2 (volume ratio)), whereby 49 mg of 1-methyl-3-difluoromethylpyrazole-4-carboxylic acid ethyl ester was obtained. This product was confirmed (identified) by NMR (Nuclear Magnetic Resonance), mass spectrometry, and the like.

[Apparatus Used and Measurement Condition]
NMR apparatus: AVANCE300 (trade name) manufactured by Bruker Corporation
Measurement solvent: $CDCl_3$
Measurement temperature: 20° C.
$^1$H-NMR δ: 7.90 (s, 1H), 7.10 (t, J=54 Hz, 1H), 4.31 (q, J=7.2 Hz, 2H), 3.97 (s, 3H), 1.36 (t, =7.2 Hz, 3H)
MS: 205.2 ($M^+$)

—Measurement of Yield and Evaluation of Selectivity—

The supernatant (1 mL) of the diluted solution described above and a standard substance (benzene-1,3,5-tricarboxylic acid triethyl ester) were weighed accurately in a 20 mL volumetric flask and diluted with acetonitrile. This solution was measured by UPLC (trade name, Ultra Performance LC, manufactured by Waters Corporation), and the area intensity (the ratio and the molar light absorption coefficient ratio separately determined at the detection wavelength of each pure product) was compared with that of the standard substance to calculate the yields of a 1-N-methyl-3-difluoromethylpyrazole compound (described as "UPLC yield (1)" in Table below) and a positional isomer (1-N-methyl-5-difluoromethylpyrazole compound (described as "UPLC yield (1')" in Table below) thereof (based on the compound (2)). In addition, regarding the selectivity of the compound (1), as the ratio (isomer ratio) of the yield of the compound (1) to the yield of the compound (1'), the ratio ((1)/(1')) of the UPLC yield (1) to the UPLC yield (1') was calculated and evaluated (The UPLC yield (1') was calculated on the assumption that the molar light absorption coefficient at the detection wavelength was equal to that of the compound (1).). The results are shown in the "UPLC yield" column and the "selectivity" column of Table 1.

[Apparatus Used and Measurement Condition]

UPLC apparatus: ACQUITY UPLC (trade name) system manufactured by Waters Corporation Column: ACQUITY UPLC (trade name) BEH C18 (particle diameter: 1.7 μm) column manufactured by Waters Corporation, diameter 2.1 mm×length 30 mm Column temperature: 40° C.

Detector: UV detector (detection wavelength: 223 nm)

Gradient condition: The composition of 0.5% formic acid aqueous solution/acetonitrile as the eluent was changed from 95/5 to 5/95 over 5 minutes. The composition of the eluent is a volume ratio.

Flow rate: 0.50 mL/min

—Confirmation of Compound Represented by Formula (5) or (6)—

A compound represented by Formula (5) or (6) was synthesized under the same conditions as in Example 8 shown in Table 1 as described below, and confirmed by NMR, mass spectrometry, and the like.

That is, a solution in which a 37% aqueous formalin (the compound (4), 164.3 mg) solution and dimethoxyethane (hereinafter, referred to as DME) (0.3 mL) were mixed and a solution of ethyl 4,4-difluoroacetoacetate (the compound (2), 337.2 mg) in a DME (0.3 mL) solution were added dropwise in order to a DME (1.7 mL) solution of methylhydrazine (the compound (3), 109 mg) at 5° C. The mixture solution was then stirred at 50° C. for 1 hour. The obtained reaction solution was cooled to room temperature and then subjected to column chromatography (eluent: ethyl acetate/hexane=1/5 (volume ratio)→ethyl acetate/hexane/methanol=5/2/1 (volume ratio)). 100 mg of a component having an Rf value of about 0.08 (developing solvent: ethyl acetate/hexane=1/2 (volume ratio)) and 15 mg of a component having an Rf value of about 0.7 (developing solvent: ethyl acetate/hexane=1/2 (volume ratio)) were isolated and purified, and then the structures were confirmed. As a result, the former was 1-methyl-3-difluoromethyl-3-hydroxypyrazolidine-4-carboxylic acid ethyl ester, which corresponds to the compound (5), and the latter was 1-methyl-3-difluoromethyl-4,5-dihydropyrazole-4-carboxylic acid ethyl ester, which corresponds to the compound (6).

[Apparatus Used and Measurement Condition]

NMR apparatus: AVANCE300 (trade name) manufactured by Bruker Corporation

Measurement solvent: $CDCl_3$

Measurement temperature: 20° C.

—Component Having an Rf Value of about 0.08 (Developing Solvent: Ethyl Acetate/Hexane=1/2)—

$^1$H-NMR δ: 5.28 (t, J=55 Hz, 1H), 4.49 (bs, 1H), 4.38-4.16 (m, 2H), 3.46 (t, J=9.0 Hz, 1H), 3.25 (d, J=9.0 Hz, 2H), 2.55 (s, 3H), 1.31 (t, J=6.9 Hz, 3H)

MS: 225.2 ($M^r$)

Component Having an Rf Value of about 0.7 (Developing Solvent: Ethyl Acetate/Hexane=1/2)—

$^1$H-NMR δ: 6.41 (t, J=54 Hz, 1H), 4.28-4.18 (m, 2H), 4.08-3.98 (m, 1H), 3.62-3.49 (m, 2H), 2.93 (s, 3H), 1.30 (t, J=7.2 Hz, 3H)

—Synthesis of Compound Represented by Formula (1A)—

Apart from the synthesis of the compound represented by Formula (1), a compound represented by Formula (1A) was synthesized as follows.

(Synthesis Example of Compound Represented by Formula (1A))

A solution in which methylhydrazine (the compound (3), 0.56 g) and 1.0 mL of diglyme were mixed and a solution in which a 37% aqueous formalin (the compound (4), 0.81 g) solution and 1.0 mL of diglyme were mixed were added dropwise in order to a diglyme (8.5 mL) solution of ethyl 4,4-difluoroacetoacetate (the compound (2), 1.67 g) at 5° C. and stirred at 50° C. for 1.5 hours, thereby obtaining a cyclocondensation intermediate mixture solution. Next, a solution obtained by mixing potassium persulfate (potassium peroxydisulfate, 4.1 g) and concentrated sulfuric acid (1.95 g) in dimethylformamide (42 mL) were added to the obtained cyclocondensation intermediate mixture, and the resultant mixture was further stirred at 50° C. for 30 minutes to carry out an oxidation reaction. To this solution, 250 mL of ethyl acetate and 250 mL of 1N aqueous hydrochloric acid were added, well stirred, and then separated. The organic layer was washed with each of 200 mL of saturated sodium hydrogen carbonate solution and 200 mL of saturated saline, and the organic phase was concentrated under reduced pressure. The concentrated residue was purified by column chromatography (eluent: ethyl acetate/hexane=1/2 (volume ratio)), whereby a mixture of 1.3 g (63%) of 1-methyl-3-difluoromethylpyrazole-4-carboxylic acid ethyl ester and 0.9 g of diglyme was obtained.

This mixture was diluted with 10 mL of ethanol, a 10% aqueous sodium hydroxide solution was added thereto, and the resultant mixture was stirred at 60° C. for 3 hours. After the concentration under reduced pressure, the reaction solution was completely dissolved in 20 mL of water, 1.5 nit of concentrated aqueous hydrochloric acid was added, and then the mixture was stirred at 5° C. for 30 minutes. The precipitated crystals were filtered, washed with water, and dried to obtain 0.8 g of 1-methyl-3-difluoromethylpyrazole-4-carboxylic acid (hydrolysis process yield: 72%).

NMR apparatus: AVANCE300 (trade name) manufactured by Bruker Corporation

Measurement solvent: DMSO-d6

Measurement temperature: 20° C.

$^1$H-NMR δ: 8.34 (s, 1H), 7.21 (t, J=54 Hz, 1H), 3.91 (s, 31-1)

Examples 1 to 3, 5 to 13, and Comparative Examples 1 to 3

The cyclocondensation reaction and the oxidation reaction were performed in the same manner as in "(Synthesis of compound represented by Formula (1))" in Example 4, except that the reaction conditions such as the raw material compounds used, the charging ratio (the charging ratio of the compounds not shown in Table 1 are the same as those in Example 4), the reaction solvent, and the presence or absence of the catalyst or the reaction solvent in "(Synthesis of compound represented by Formula (1))" in Example 4, were changed as shown in Table 1. With respect to the obtained diluted solution, the yield and isomer ratio of each compound were calculated in the same manner as in Example 4, and the results are shown in Table 1.

The reaction scheme and results in Examples and Comparative Examples are shown below. In this reaction scheme and Table 1, $R^1$ and $R^2$ are as shown in Table 1, Me indicates methyl, Et indicates ethyl, DMF indicates N,N-dimethylformamide, THF indicates tetrahydrofuran, t-Bu indicates tert-butyl, DME indicates dimethyl ether, and c. HCl indicates 12M HCl. In addition, in the "reaction solvent" column of Table 1, the description of water and methanol which are derived from formalin is omitted. The "catalyst" column describes the name of the catalyst used and the amount used, and the number indicating the amount used indicates the molar equivalent ratio of the acid catalyst or base catalyst used to the compound (2). In addition, "-" indicates that neither an acid catalyst nor a base catalyst was added.

addition, in a case where only ethanol was used as the solvent, the yield of the target product was 39.1% in Comparative Example 2 in which the reaction time was 1 hour, and the yield of the target product was 23.6% in Comparative Example 3 in which the reaction time was 2 hours and the selectivity was 5.1. Accordingly, Examples 2 and 3 showed lower yields and were inferior as the producing method (Example 5 in which the synthesis was performed under the same conditions as in Comparative

TABLE 1

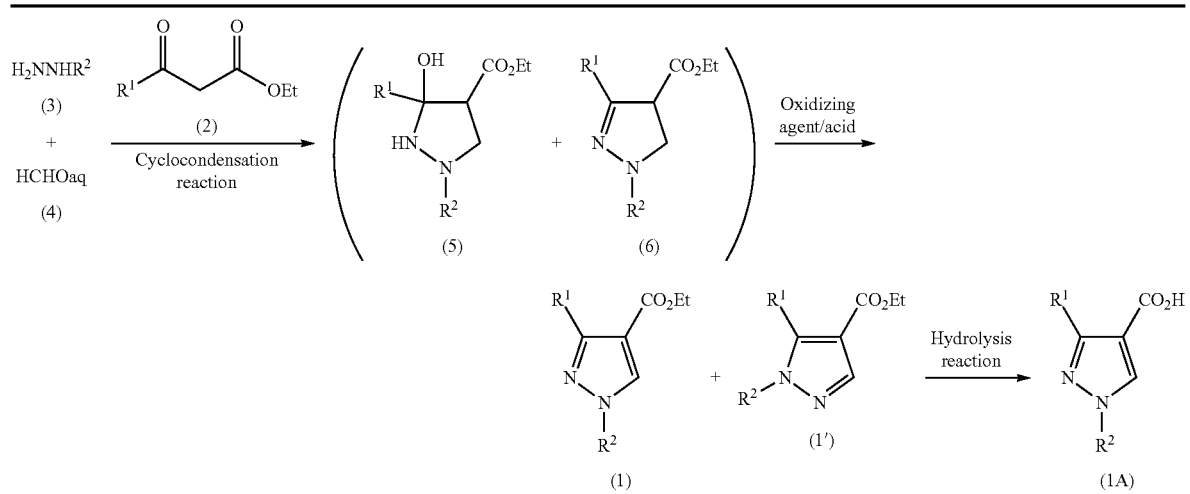

| | | | Molar equivalent ratio of | | | Synthesis conditions of compound (1) | | UPLC yield | | |
|---|---|---|---|---|---|---|---|---|---|---|
| | | | $H_2NNHR^2$ to the compound (2) | Reaction solvent | Catalyst/ amount used | Oxidizing agent/acid | Reaction temperature/ reaction time | (1) [%] | (1') [%] | Selectivity (1)/(1') |
| | $R^1$ | $R^2$ | | | | | | | | |
| Example 1 | $CF_2H$ | Me | 1.0 | DMF | — | $K_2S_2O_8/H_2SO_4$ | 50° C./0.5 h | 43.9 | 6.3 | 7.0 |
| Example 2 | $CF_2H$ | Me | 1.0 | THF | — | $K_2S_2O_8/H_2SO_4$ | 50° C./0.5 h | 57.6 | 9.0 | 6.4 |
| Example 3 | $CF_2H$ | Me | 1.0 | tBuOMe | — | $K_2S_2O_8/H_2SO_4$ | 50° C./0.5 h | 53.0 | 7.5 | 7.1 |
| Example 4 | $CF_2H$ | Me | 1.0 | Diglyme | — | $K_2S_2O_8/H_2SO_4$ | 50° C./0.5 h | 63.1 | 8.8 | 7.2 |
| Example 5 | $CF_2H$ | Me | 1.0 | Diglyme | — | $K_2S_2O_8/H_2SO_4$ | 50° C./0.5 h | 54.8 | 7.7 | 7.1 |
| Example 6 | $CF_2H$ | Me | 1.1 | Diglyme | — | $K_2S_2O_8/H_2SO_4$ | 50° C./0.5 h | 61.5 | 6.0 | 10.3 |
| Example 7 | $CF_2H$ | Me | 1.2 | Diglyme | — | $K_2S_2O_8/H_2SO_4$ | 50° C./0.5 h | 63.8 | 5.4 | 11.8 |
| Example 8 | $CF_2H$ | Me | 1.2 | DME | — | $K_2S_2O_8/H_2SO_4$ | 50° C./0.5 h | 59.9 | 4.9 | 12.2 |
| Example 9 | $CF_2H$ | Me | 1.3 | Diglyme | — | $K_2S_2O_8/H_2SO_4$ | 50° C./0.5 h | 60.8 | 4.6 | 13.2 |
| Example 10 | $CF_2H$ | Me | 1.0 | Diglyme/EtOH = 1/1 | — | $K_2S_2O_8/H_2SO_4$ | 50° C./0.5 h | 57.7 | 5.7 | 10.1 |
| Example 11 | $CF_2H$ | Me | 1.0 | Diglyme/EtOH = 1/1 | — | $K_2S_2O_8/H_2SO_4$ | 50° C./0.5 h | 52.8 | 5.2 | 10.2 |
| Example 12 | $CF_2H$ | Me | 1.0 | Diglyme | $Et_3N$/0.2 | $K_2S_2O_8/H_2SO_4$ | 50° C./0.5 h | 46.0 | 5.8 | 7.9 |
| Example 13 | $CF_2H$ | Me | 1.0 | Diglyme | c.HCl/0.2 | $K_2S_2O_8/H_2SO_4$ | 50° C./0.5 h | 32.7 | 4.7 | 7.0 |
| Comparative Example 1 | $CF_3$ | Me | 1.2 | Diglyme | — | $K_2S_2O_8/H_2SO_4$ | 50° C./0.5 h | 27.7 | 9.9 | 2.8 |
| Comparative Example 2 | $CF_2H$ | Me | 1.0 | EtOH | — | $K_2S_2O_8/H_2SO_4$ | 50° C./0.5 h | 39.1 | 4.2 | 9.3 |
| Comparative Example 3 | $CF_2H$ | Me | 1.0 | EtOH | — | $K_2S_2O_8/H_2SO_4$ | 50° C./0.5 h | 23.6 | 4.6 | 5.1 |

Note: Reaction temperature/reaction time for the cyclocondensation step: 50° C./2 h for Examples 1-4 and 11, 50° C./1 h for Examples 5-10, 12, 13, and Comparative Examples 1-2; 50° C./2 h for Comparative Example 3.

As shown in Table 1, in Comparative Example 1 in which the 3-trifluoromethylpyrazole compound was synthesized, the yield of the corresponding target compound (1) was 27.7% and the selectivity (isomer ratio) was 2.8, both of which were low, and thus was inferior as the producing method (Example 7 in which the 3-difluoromethylpyrazole compound was synthesized under the same conditions as in Comparative Example 1 showed a yield of 63.8% and a selectivity of 11.8 which was higher than expected). In Example 2 using the reaction solvent specified in the present invention showed a yield of 54.8% and a selectivity of 7.1. In addition, Examples 1 to 4 in which the synthesis was performed under the same conditions as in Comparative Example 3 using the reaction solvent specified in the present invention showed a yield of 43.9 to 63.1% and a selectivity of 6.4 to 7.2).

On the other hand, in Examples 1 to 13 in which the 3-difluoromethylpyrazole compound represented by Formula (1) was synthesized by the producing method for a carboxylic acid compound precursor of the embodiment of the present invention, the 3-difluoromethylpyrazole compound represented by Formula (1), which is the target product, could be easily produced from inexpensive raw materials under mild reaction conditions with a good yield of about 44% or more in total and an excellent selectivity of 6.4 or more. In particular, in a case where the pyrazole compound precursor is oxidized without isolation or purification from the precursor solution, the effect of improving the yield is enhanced.

As described above, the present invention can provide producing methods for a 3-difluoromethylpyrazole compound and a 3-difluoromethylpyrazole-4-carboxylic acid compound, in particular, which are industrially suitable.

According to the producing method of the embodiment of the present invention, the targeted 3-difluoromethylpyrazole compound and 3-difluoromethylpyrazole-4-carboxylic acid compound can be produced in good yield and high selectivity (while suppressing the generation of positional isomers in the cyclocondensation reaction) with simple operation under mild conditions, using the compound (2), the compound (3), and formaldehyde as raw materials, which are relatively inexpensive and easily available compounds. Therefore, the present invention is highly valuable in industrial utility. In particular, both compounds obtained in the present invention are useful as intermediates for the pharmaceutical and agricultural chemicals, and examples of such a pharmaceutical and an agricultural chemical include bixaphen, fluxapyroxad, and pydiflumetofen.

In addition, the producing method according to the embodiment of the present invention can provide a useful synthetic intermediate.

The present invention has been described together with the embodiments of the present invention. However, the inventors of the present invention do not intend to limit the present invention to any of the details of the description unless otherwise specified, and it is considered that the present invention should be broadly construed without departing from the spirit and scope of the invention shown in the attached "WHAT IS CLAIMED IS".

This application claims priority based on JP2018-096387 filed in Japan on May 18, 2018, which is incorporated herein by reference as a part of the description of the present specification.

What is claimed is:

1. A method for preparing a 3-difluoromethylpyrazole compound represented by Formula (1), said method comprising:

in a reaction solvent containing at least one selected from Solvent group <I>,
subjecting a compound represented by Formula (2), a hydrazine compound represented by Formula (3), and formaldehyde to a cyclocondensation reaction; and
subsequently oxidizing the obtained pyrazole compound precursor,

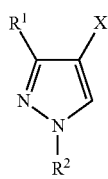

(1)

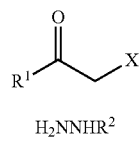

(2)

(3)

wherein $R^1$ represents —$CF_2H$, $R^2$ represents a hydrogen atom, an alkyl group, an aryl group, or a heteroaryl group, and X represents —CN, —$COOR^3$, or —$CONR^4R^5$, where $R^3$ represents an alkyl group, and $R^4$ and $R^5$ represent a hydrogen atom or an alkyl group, Solvent group <I>
an amide solvent, a urea solvent, a nitrile solvent, an ether solvent, a sulfoxide solvent, a sulfone solvent, an ester solvent, a hydrocarbon solvent, a halogen solvent, and a ketone solvent.

2. The method according to claim 1, wherein the pyrazole compound precursor includes a compound represented by Formula (5) or a compound represented by Formula (6),

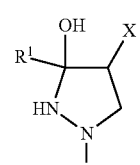

(5)

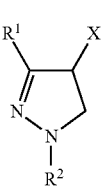

(6)

wherein $R^1$, $R^2$, and X respectively have the same meanings as $R^1$, $R^2$, and X in Formula (1).

3. The method according to claim 1, wherein the pyrazole compound precursor is oxidized using a persulfate under an acidic condition.

4. The method according to claim 1, wherein the pyrazole compound precursor is oxidized without isolating or purifying from a precursor solution obtained by the cyclocondensation reaction.

5. The method according to claim 1, wherein the cyclocondensation reaction is carried out in the absence of an acid catalyst and a base catalyst.

6. A method for preparing a 3-difluoromethylpyrazole-4-carboxylic acid compound represented by Formula (1A), said method comprising:

converting X in a 3-difluoromethylpyrazole compound obtained by the method of claim 1 to —COOH,

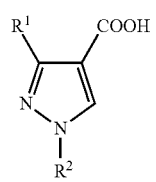

(1A)

wherein $R^1$ and $R^2$ respectively have the same meanings as $R^1$ and $R^2$ in Formula (1).

7. A pyrazolidine compound represented by Formula (5),

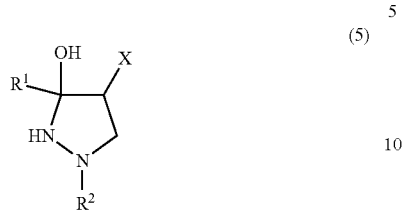

(5)

wherein $R^1$ represents —$CF_2H$, $R^2$ represents a hydrogen atom, an alkyl group, an aryl group or a heteroaryl group, and X represents —CN, —$COOR^3$ or —$CONR^4R^5$, where $R^3$ represents an alkyl group, and $R^4$ and $R^5$ represent a hydrogen atom or an alkyl group.

8. The pyrazolidine compound according to claim 7, wherein the $R^2$ is an alkyl group, and X is —$COOR_3$.

* * * * *